United States Patent [19]

Pulliainen et al.

[11] Patent Number: 5,518,591
[45] Date of Patent: May 21, 1996

[54] USE OF ELECTRODE SYSTEM FOR MEASURING HYDROGEN PEROXIDE CONCENTRATION

[75] Inventors: Martti Pulliainen, Anttola; Timo Laurila, Tampere; Hannu Savisalo, Mikkeli, all of Finland

[73] Assignee: Conrex Automation Oy, Mikkeli, Finland

[21] Appl. No.: 292,373

[22] Filed: Aug. 18, 1994

[30] Foreign Application Priority Data

Aug. 20, 1993 [FI] Finland ................................. 933667

[51] Int. Cl.⁶ .................................................. G01N 27/26
[52] U.S. Cl. ...................... 205/782; 436/150; 205/775.5
[58] Field of Search ................................. 204/412, 400, 204/153.1, 292, 403, 153.12, 153.11; 436/150

[56] References Cited

U.S. PATENT DOCUMENTS

| 4,172,770 | 10/1979 | Semersky et al. | 204/412 |
| 4,564,422 | 1/1986 | Simoneau et al. | 204/400 |
| 4,687,997 | 8/1987 | Tao | 204/130 |
| 4,933,292 | 6/1990 | Savisalo et al. | 436/150 |
| 5,135,623 | 8/1992 | Dziabo et al. | 204/131 |

FOREIGN PATENT DOCUMENTS 80526  3/1988  Finland.

*Primary Examiner*—Bruce F. Bell
*Attorney, Agent, or Firm*—Steinberg, Raskin & Davidson

[57] ABSTRACT

An electrode system and method, including a measurement electrode, a reference electrode and a counterelectrode, for measuring hydrogen peroxide concentration in a solution. For the measurement electrode, an electrode made from titanium, zirconium, tantalum or niobium is used.

7 Claims, 10 Drawing Sheets

USE OF ELECTRODE SYSTEM FOR MEASURING HYDROGEN PEROXIDE CONCENTRATION

BACKGROUND OF THE INVENTION

The present invention relates to the use of an electrode system, comprising a measurement electrode, a reference electrode and a counterelectrode, for measuring the concentration of hydrogen peroxide. The present invention also relates to a method for measuring the concentration of hydrogen peroxide in a solution.

With regard to the state of the art, reference is made to Finnish Patent No. 80,526 (corresponding to U.S. Pat. No. 4,933,292, the specification of which is incorporated by reference herein) which describes a method for controlling the pulping process. In the method described in this patent, an electrode system is used which comprises one or more measurement electrodes, reference electrodes and power supplying counterelectrodes, positioned in a pulp boiler. Current is supplied from a power source to the circuit so that the voltage between the measurement electrode and the reference electrode, in other words, the electrochemical potential of the measurement electrode is substantially constant, so that the current equivalent to this potential is directly proportional to the activity of the chemicals in the boiler. For the measurement electrode, coal steel, iron, copper, zinc, cadmium, or monel metal can be used. The electrochemical potential of the measurement electrode varies in the range from about −500 millivolt to about −1500 millivolt to the calomel electrode.

The concentration of hydrogen peroxide is required to be measured, inter alia, from the bleaching pulp. A change in the hydrogen peroxide concentration influences a variety of factors in the solution. Such factors are, among other things, the idle potential of the measurement electrode, the current densities measured on the polarization curve, and the zero point of the polarization curve, pH, the conductivity of the solution, and temperature.

The difference of potential between the measurement electrode and the electrolytic solution, when measured in relation to the reference electrode, i.e., the idle potential of the measurement electrode, changes as a function of the hydrogen peroxide content in the solution. The direction and intensity of the change is dependent on the electrode material used. When an inert material, such as platinum, is used for the measurement electrode, the measurement mentioned above yields a so-called redox potential. The redox potential is a potential difference characteristic of the solution, and caused by redox reactions on the surface of the electrode, thereby measuring the oxidation capacity of the solution The redox potential behaves when compared with the idle potential of an electrode made of a less noble material, less actively because the dissolving metal ion is non-existent.

An electrode arrangement according to Finnish Patent No. 80,526 is used in which a platinum electrode is used as the measurement electrode for measuring the hydrogen peroxide content in a solution. However, the use of a platinum electrode for the measurement electrode provides a relatively inaccurate dependency on the hydrogen peroxide concentration because in the polarization curves, it can be seen that a change in the current density divided by a change of the concentration, i.e. the ratio $\Delta I/\Delta C$, is too low for accurate measurement of the hydrogen peroxide concentration. In addition, the soilings of the electrodes generate inaccuracy in measurement results.

OBJECTS AND SUMMARY OF THE INVENTION

It is an object of the present invention to provide an improvement in the measurement methods and apparatus which measure the concentration of hydrogen peroxide, e.g., in solutions.

Accordingly, in the invention, for the measurement electrode, an electrode is used, in a measurement system including a reference electrode and counterelectrode, which is selected from the group consisting of titanium, zirconium, tantalum and niobium.

In this manner, i.e., by using a measurement electrode composed of at one of these materials, e.g., a titanium electrode, in a system which measures the concentration of hydrogen peroxide, the corrosion of the measurement electrode is highly sensitive to the hydrogen peroxide concentration. Therefore, the ratio $\Delta I/\Delta C$ is adequate and a high accuracy is obtained in measuring the hydrogen peroxide concentration of the solution in which the measurement electrode is applied.

The method in accordance with the invention for measuring the concentration of hydrogen peroxide in a solution, comprises the steps of coupling a measurement electrode, a reference electrode and a counterelectrode with the solution, and providing the measurement electrode as an electrode selected from the group consisting of titanium, zirconium, tantalum and niobium. Preferably, measurement means such as a potentiometer is coupled to the measurement electrode, the reference electrode and the counterelectrode, and the electrochemical potential of the measurement electrode which correlates to the concentration of hydrogen peroxide in the solution is measured by means of the potentiometer.

In the following, the invention will be described in detail with reference to an advantageous embodiment of the invention illustrated schematically in the figures in the accompanying drawings. However, the invention is by no means strictly confined to the details of this embodiment.

BRIEF DESCRIPTION OF THE DRAWINGS

The following drawings are illustrative of one embodiment of the invention and are not meant to limit the scope of the invention as encompassed by the claims.

DETAILED DESCRIPTION OF THE INVENTION

Figure 1:
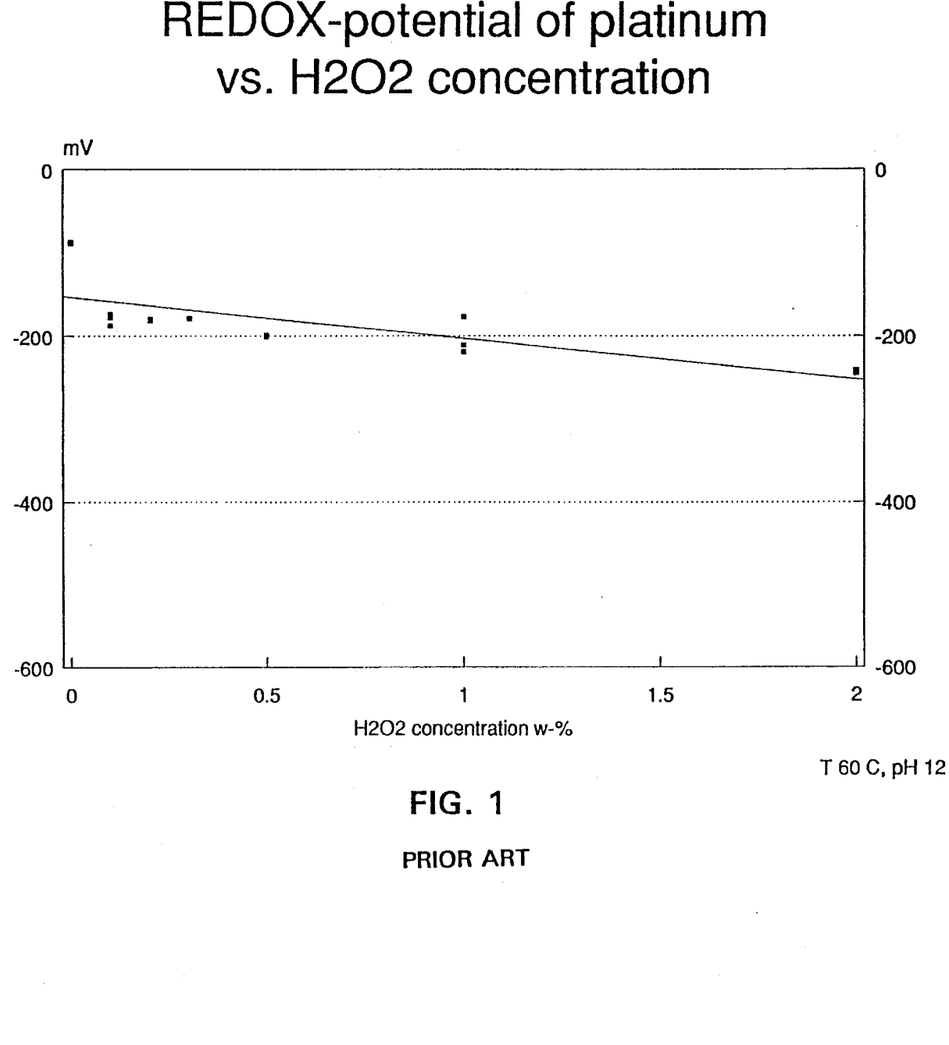
FIG. 1 illustrates the redox potential of a platinum electrode used in a design known in the prior art as a function of hydrogen peroxide concentration in a solution.

FIG. 1 presents the redox potential of the platinum electrode used in a state of art design as a function of hydrogen peroxide concentration. FIG. 1 shows that the redox potential of such a platinum electrode behaves less powerfully, i.e., has a lower slope, when compared with the idle potential of an electrode made from a less noble material (as will be discussed with reference to FIG. 3) because the dissolving metal ion is non-existent. The potential difference measurement is a standard voltage measurement which can be used after the filtering and reinforcement directly as control data.

Figure 2:
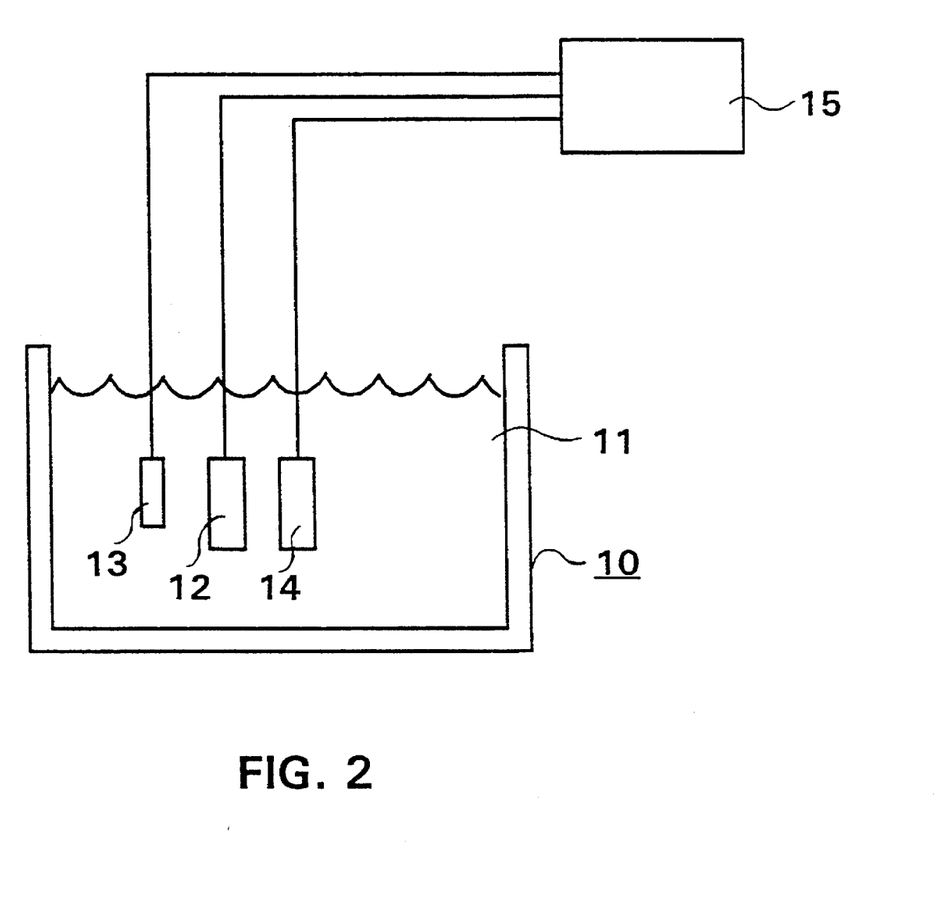
FIG. 2 illustrates an electrode arrangement in accordance with the present invention as a schematical parallel image, inserted in a container containing hydrogen peroxide.

In FIG. 2, a system in which the hydrogen peroxide concentration can be measured is shown. A container 10 is adapted to contain a solution, e.g., which comprises at least some concentration of hydrogen peroxide. A measurement electrode 12, i.e. work electrode, is inserted into the solution, a reference electrode 13 and a counterelectrode 14 are also inserted into the solution. A potentiostat or potentiometer 15 is connected to the measurement electrode 12, reference electrode 13 and counterelectrode 14 and measures the potential of the measurement electrode. The reference electrode 13 and the counterelectrode 14 can be any electrodes serving the necessary function.

Figure 3:
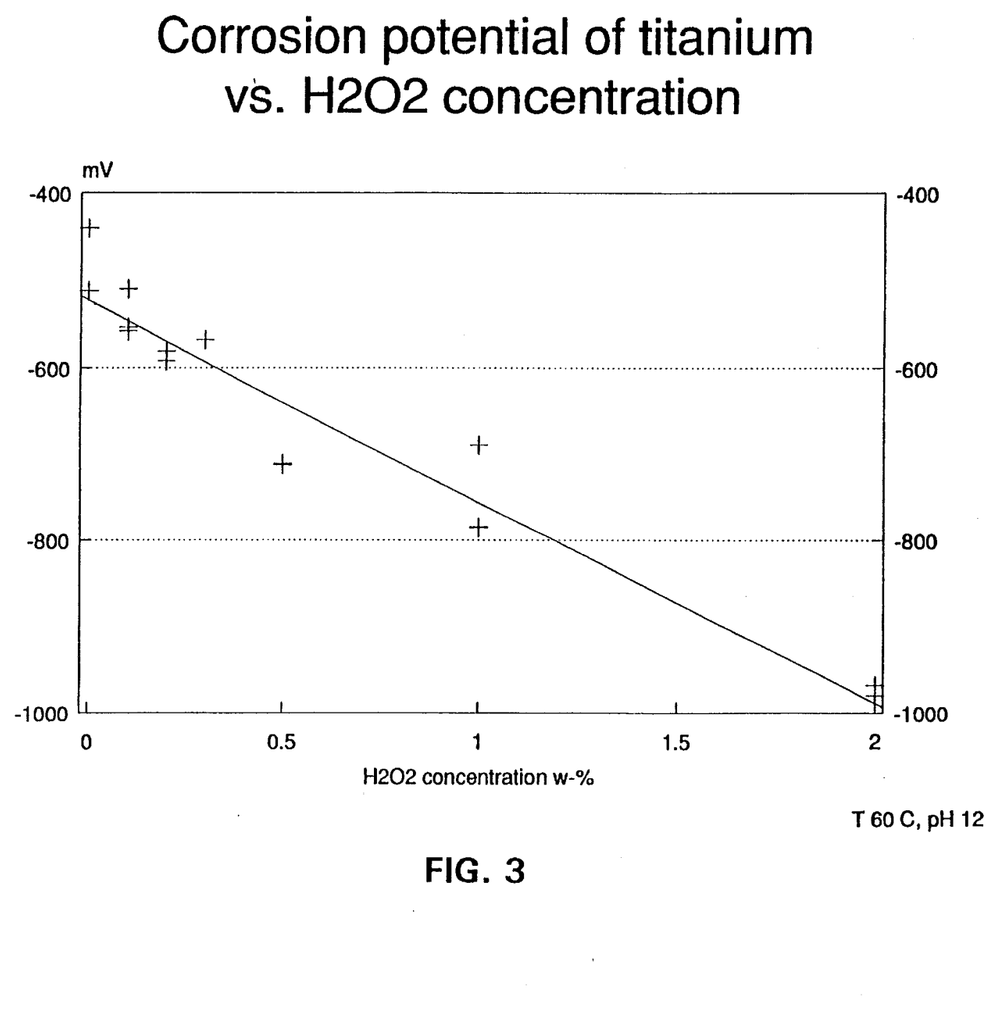
FIG. 3 illustrates the idle potential of the titanium electrode used in the electrode arrangement according to the invention, as a function of hydrogen peroxide concentration.

FIG. 3 shows that the idle potential of the titanium electrode decreases considerably, i.e., has a large slope, as the hydrogen peroxide concentration increases (from 0% of the solution to about 2% of the solution) when the pH is maintained constant. An essentially similar property is found also in zirconium, tantalum and niobium electrodes.

Figure 4A:
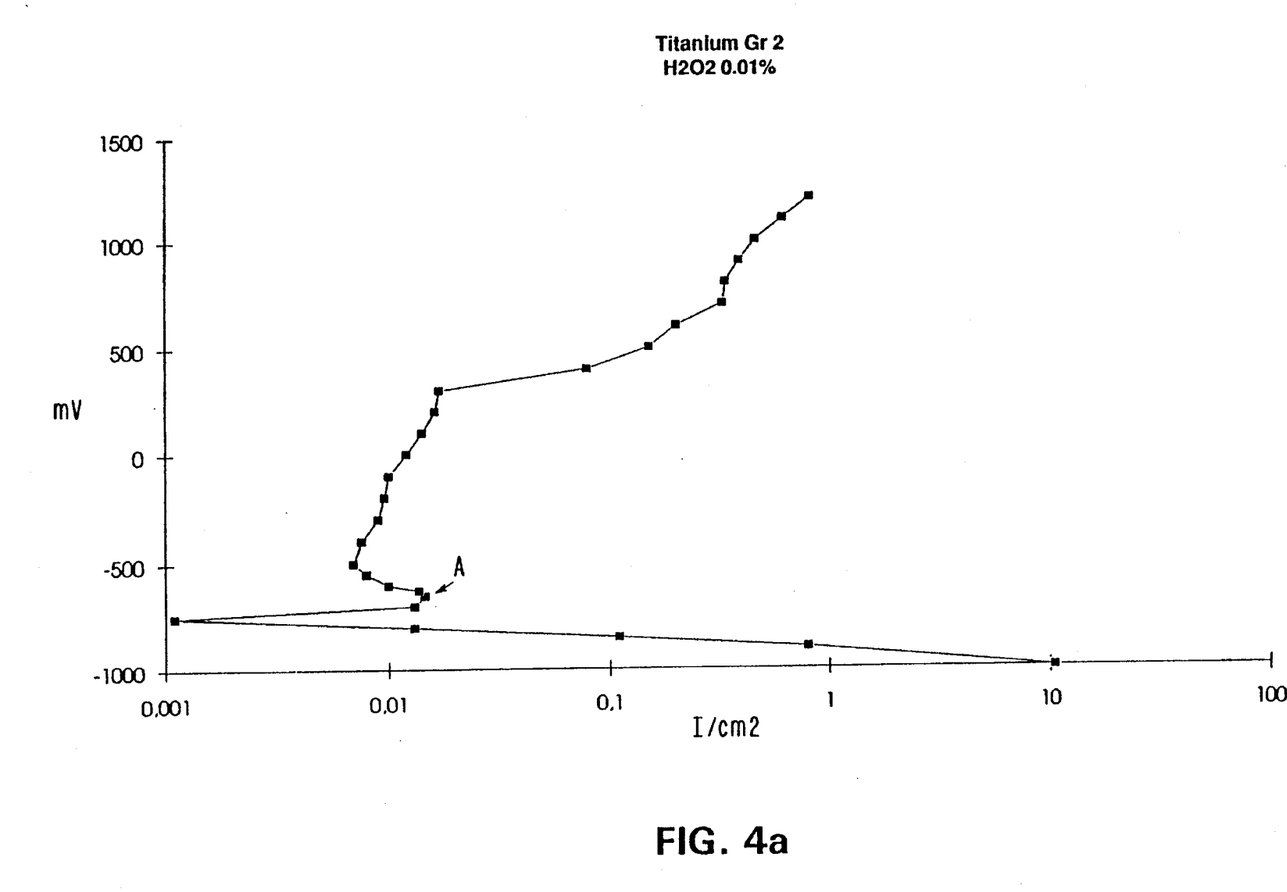
FIGS. 4a–4c illustrate polarization curves of the titanium electrode as a function of hydrogen peroxide concentration.
Figure 4B:
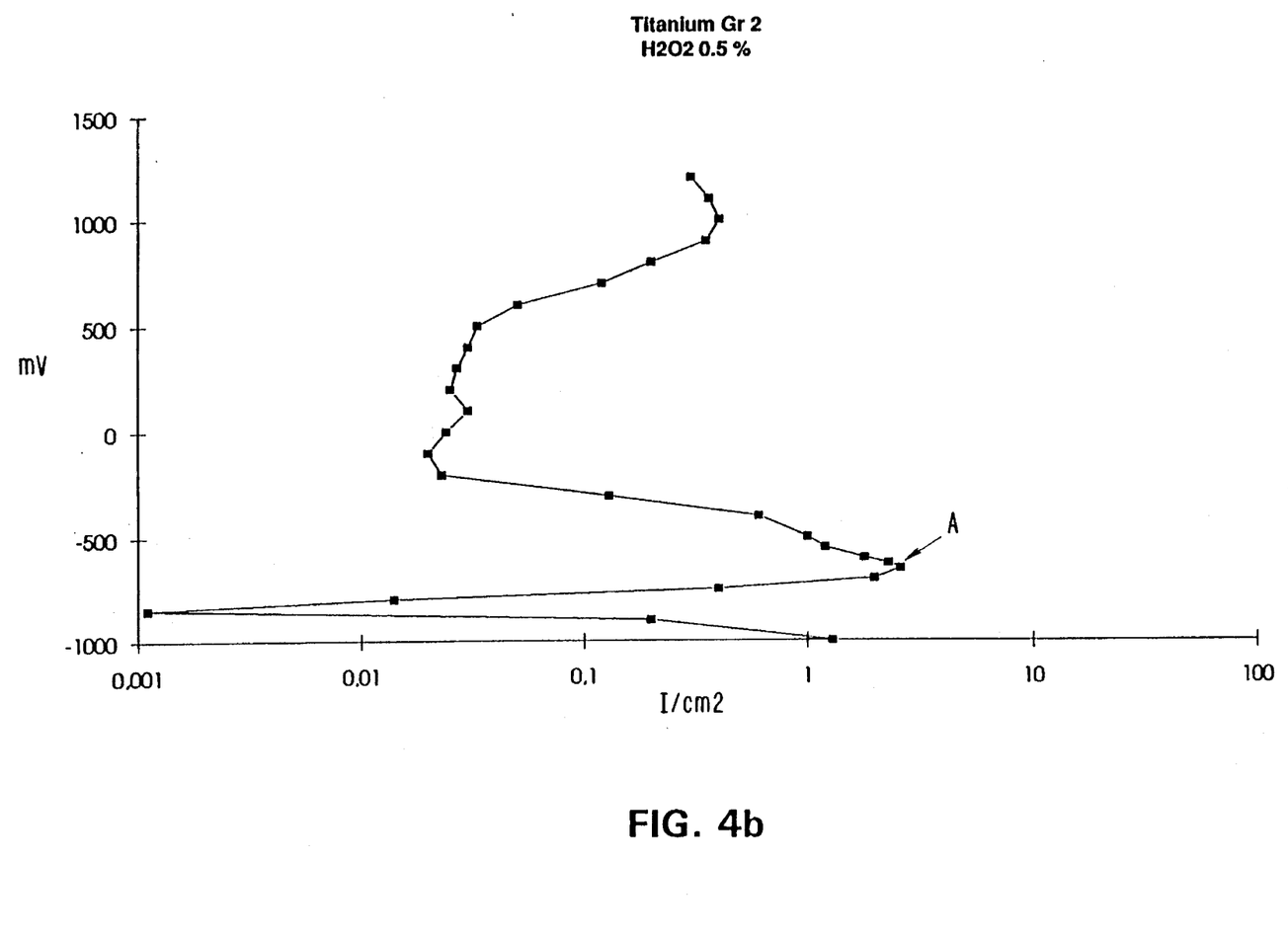
Figure 4C:
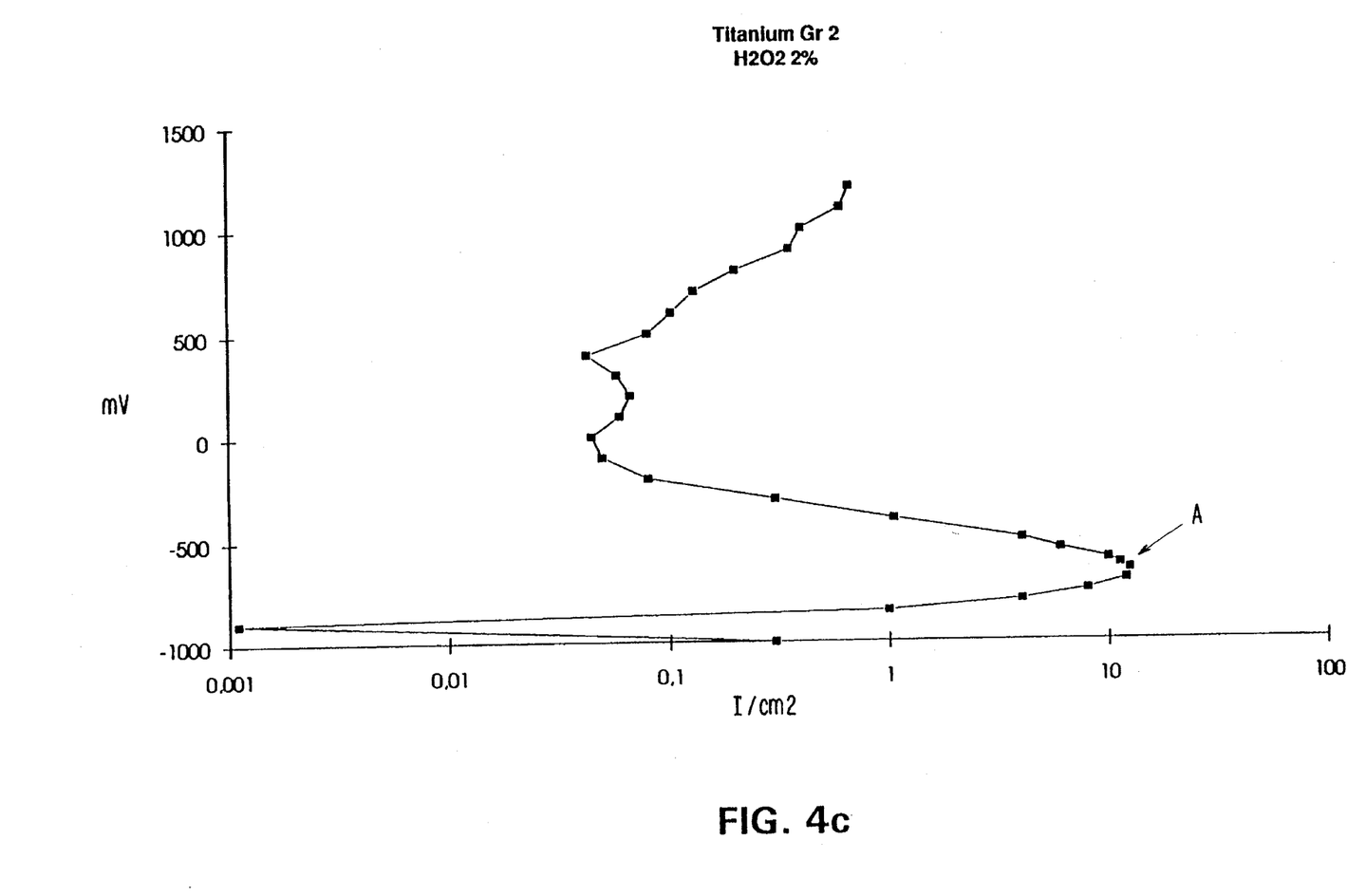

FIGS. 4a–4c show that the current density maximum A indicating strong corrosion increases as a function of hydrogen peroxide concentration. When an electrode, selected from the group titanium, zirconium, tantalum and niobium, is used as a measurement electrode, the corrosion rate of the electrode materials correlates to a sufficient degree with the hydrogen peroxide concentration, whereby adequate accuracy is obtained in measuring the hydrogen peroxide concentration. Thus, other materials having a strong corrosion rate which correlates to a sufficient degree with the hydrogen peroxide concentration may also be used in accordance with the invention.

In according with the invention, a measurement electrode of titanium, zirconium, tantalum or niobium can be implemented using all corrosion rate measurement methods known in the art, such as Tafel extrapolation, linear polarization, measurement of the corrosion potential of electrode, etc.

Figure 5:
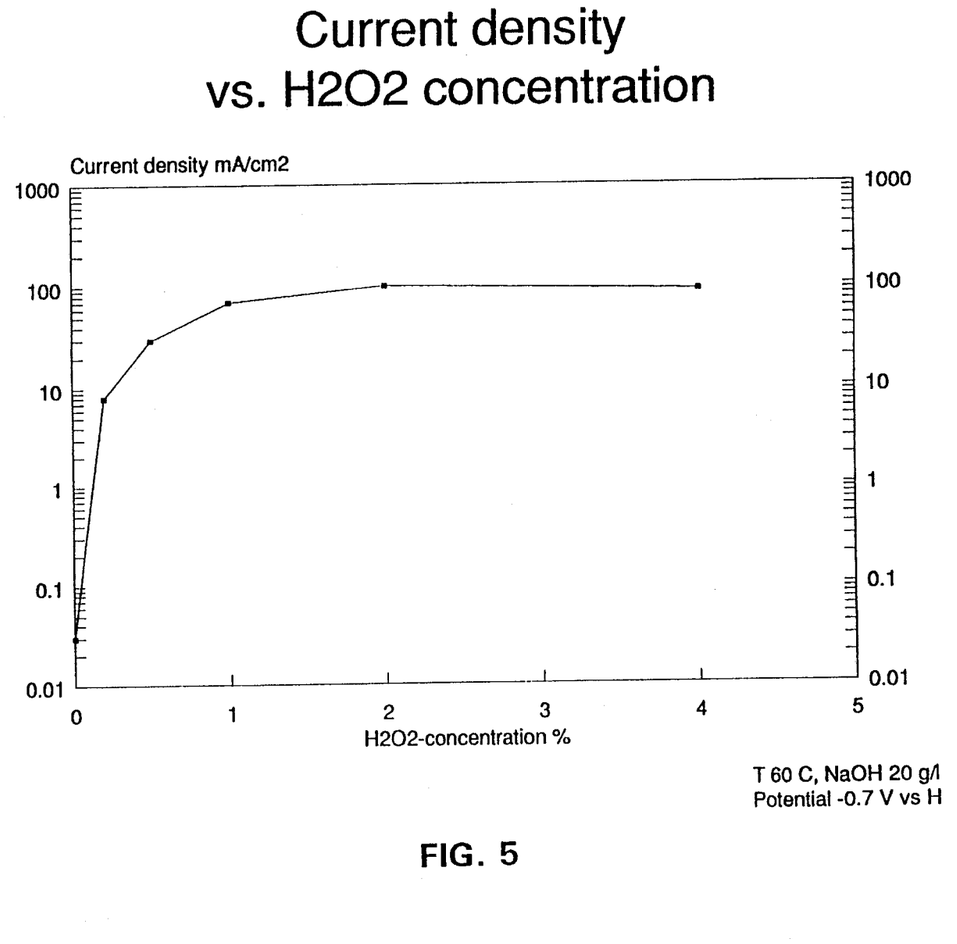
FIG. 5 graphically illustrates the dependency of the current density formed from a plurality of measured polarization curves of an electrode arrangement in accordance with the invention on the hydrogen peroxide concentration.

The curve ΔI/ΔC shown in FIG. 5 yields information about the density of a net current of the circuit produced by an external power source, a current supply electrode, the solution and the sample electrode, calculated for the surface area unit of the sample electrode as a function of the hydrogen peroxide concentration. The changes caused in the properties of the solution and on the surface of the sample electrode by the hydrogen peroxide concentration are extremely clearly visible as a change of the current density (FIG. 5) and as a displacement of the zero point of the polarization curve (FIGS. 4a–4c). The direction and strength of the change can be seen in FIG. 5 when a titanium electrode is used in running the polarization curves. The current densities have been measured when the potential is −0.7V vs. H.

On the semilogarithmic scale in FIG. 5, it can be seen that a change of the hydrogen peroxide concentration exerts an influence on the current density in the concentration range 0–2%, being e.g. in 10% precipitation mass equivalent to hydrogen peroxide batching of 0 to 200 kg per ton of absolutely dry pulp. In this range, the current density becomes thousand-fold from the initial value, so that theoretically it is possible to analyze a hydrogen peroxide concentration at 0.0002% accuracy by measuring the current at 0.1 mA accuracy.

In practice though, it is not worthwhile to run the polarization curve at a very wide area of potential. Instead, it is more sensible to concentrate on the range providing the most obvious indication and on determining the zero point. In this manner, the polarization curve can be obtained faster to run, and thus reacting in process changes is faster. The curve running frequency can be defined specifically for each application, but in practice, the minimum frequency is in general about 1 curve per minute.

It is to be noted that the above-mentioned factors are affected, in addition to the hydrogen peroxide concentration, also by pH, temperature and bulk flow rate. Thus, in the algorithm of the hydrogen peroxide concentration analyzer also the local pH, conductivity and temperature can be fed, in addition to data on the potential and current.

The process-specific differences, additive contents, running methods, etc. have also to be taken into account. Most probably each positioning requires some calibration, in the course of which the measurement results have to be compared with manual analyses.

Figure 6:
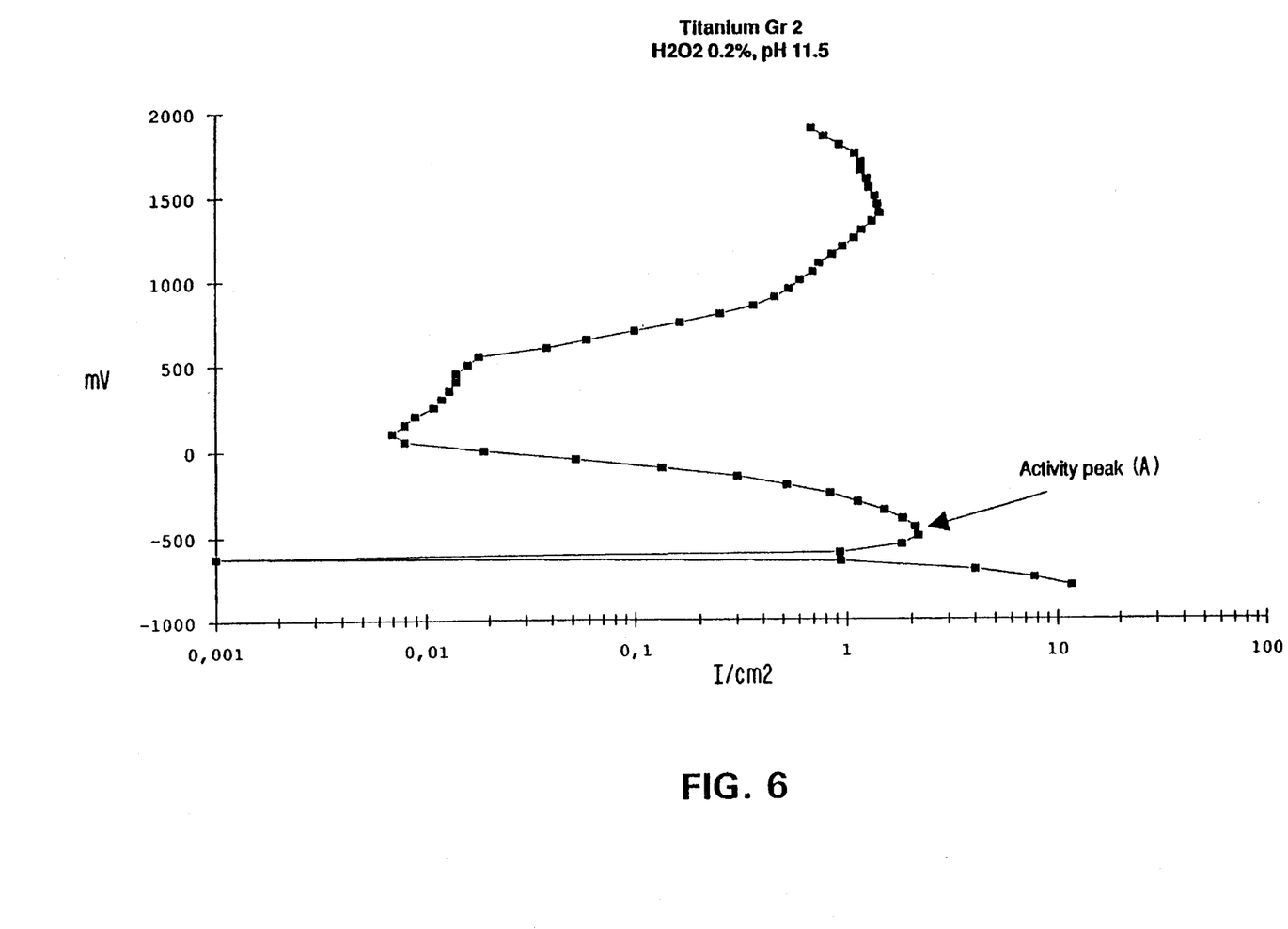
FIG. 6 graphically illustrates a polarization curve of an electrode arrangement according to the invention when the hydrogen peroxide concentration is about 0.2% and the pH of the solution in which the electrode arrangement is applied is about 11.5.
Figure 7:
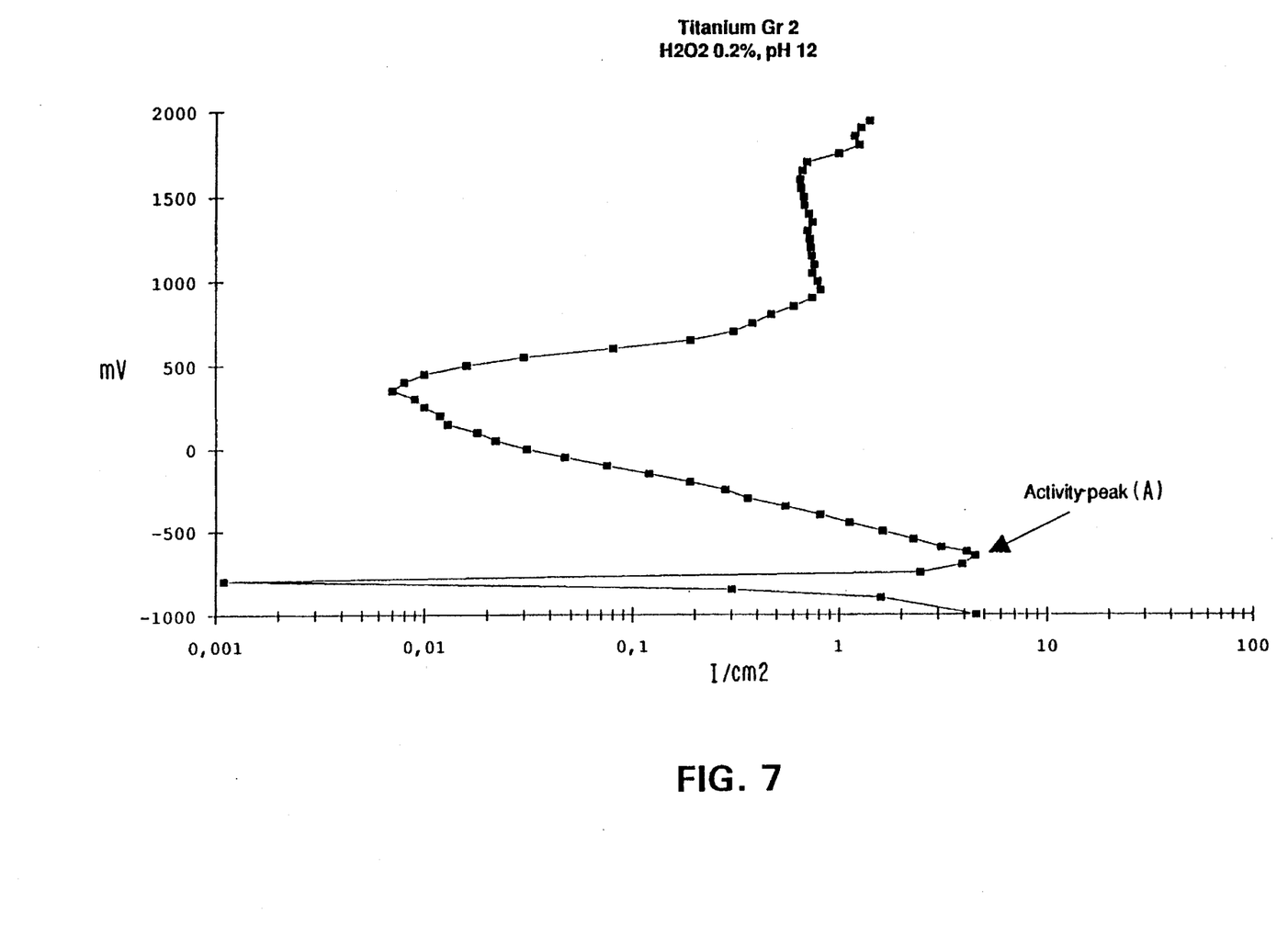
FIG. 7 graphically illustrates a polarization curve of an electrode arrangement according to the invention when the hydrogen peroxide concentration is about 0.2% and the pH of the solution in which the electrode arrangement is applied is about 12.

In FIGS. 6 and 7, a relatively strong peak can be observed at point A, indicating that the corrosion of the measurement electrode is fast. In FIGS. 6 and 7, it is possible to observe that when the hydrogen peroxide concentration in the solution is the same but when the pH values are different in magnitude, in the instance of FIGS. 6 and 7, 0.2% and when the pH of the solution is 11.5 and 12, respectively, the point of peak A on the horizontal axis changes as a function of the pH.

Figure 8:
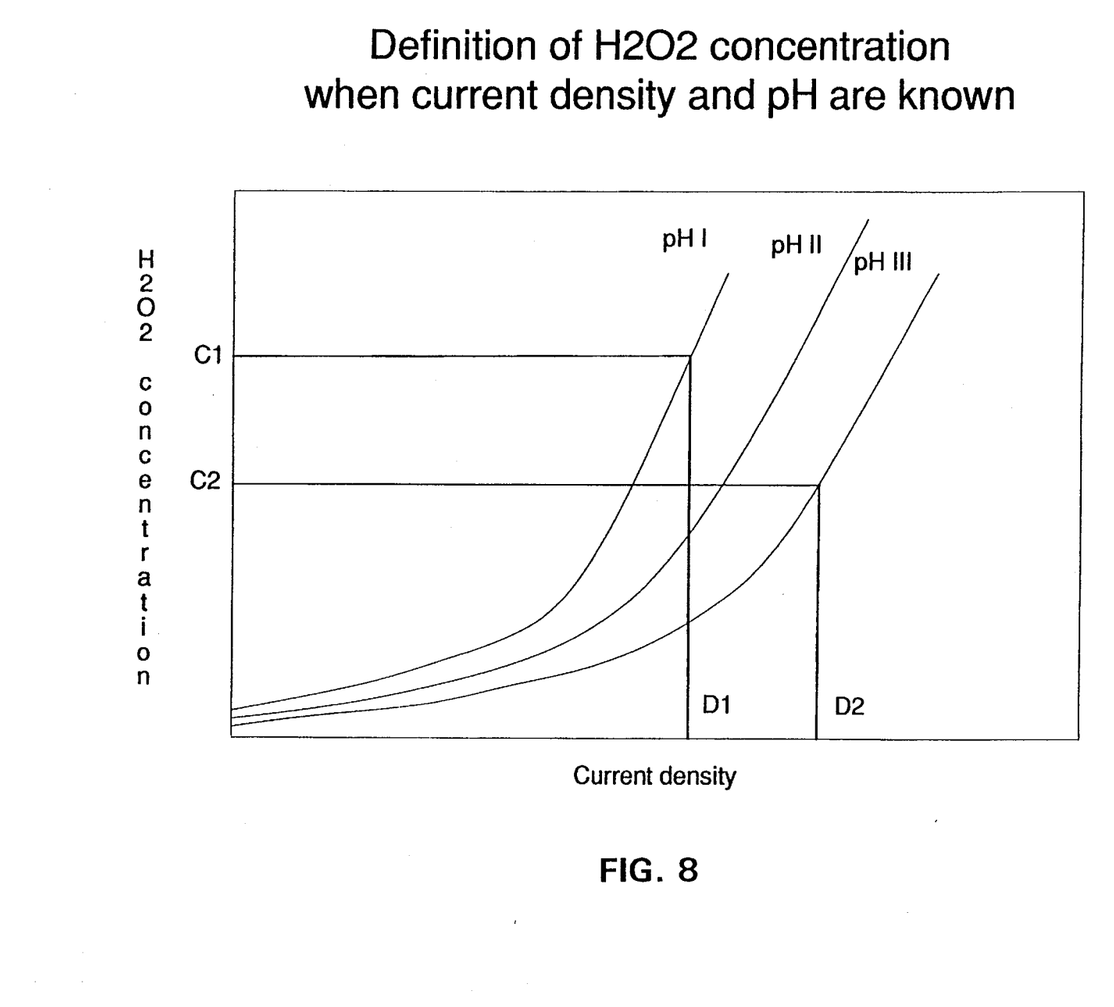
FIG. 8 shows graphically the hydrogen peroxide concentration as a function of current density at various pH values.

FIG. 8 shows graphically the concentration of the hydrogen peroxide content as a function of the current density at different pH values. When the pH of a solution is known, the content of the hydrogen peroxide can be determined with ease from the curve shown in FIG. 8.

The examples provided above are not meant to be exclusive. Many other variations of the present invention would be obvious to those skilled in the art, and are contemplated to be within the scope of the appended claims.

We claim:

1. Method for measuring the concentration of hydrogen peroxide in a solution, comprising the steps of:

coupling a measurement electrode formed from a material selected from the group consisting of titanium, zirconium, tantalum and niobium, a reference electrode and a counterelectrode with the solution containing hydrogen peroxide, maintaining a voltage between said measurement electrode and said reference electrode, measuring the rate of corrosion of said measurement electrode while hydrogen peroxide reacts with the material of said measurement electrode and causes electrochemical corrosion thereof, and determining the concentration of hydrogen peroxide from the measured corrosion rate.

2. The method of claim 1, further comprising the steps of measuring a difference between potential between said measurement electrode and the solution and potential between said reference electrode and the solution, and determining the concentration of hydrogen peroxide from the measured potential difference which correlates to the corrosion rate of said measurement electrode.

3. The method of claim 1, further comprising the steps of:

coupling a potentiometer to said measurement electrode, said reference electrode and said counterelectrode, and measuring the electrochemical potential of said measurement electrode which correlates to the concentration of hydrogen peroxide in the solution by means of said potentiometer.

4. The method of claim 1, wherein the voltage between said measurement electrode and said reference electrode is maintained substantially constant whereby the hydrogen peroxide reacts with the material of said measurement electrode and causes electrochemical corrosion thereof, further comprising the step of determining the concentration of hydrogen peroxide from a measured current density required to maintain the substantially constant voltage which correlates to the corrosion rate of said measurement electrode.

5. The method of claim 4, wherein the step of determining the concentration of hydrogen peroxide from the measured current density comprising the step of:

varying the voltage within a range of voltages in each of a plurality of solutions, each solution having a known hydrogen peroxide concentration which differs from the hydrogen peroxide concentration of the other solutions to thereby obtain polarization curves of said measurement electrode as a function of hydrogen peroxide concentration.

6. The method of claim 5, further comprising the step of determining a maximum current value from said polarization curves which correlates to the concentration of hydrogen peroxide.

7. The method of claim 5, further comprising the step of charting current density as a function of hydrogen peroxide concentration such that for a known, measured current density of the solution, the hydrogen peroxide concentration can be obtained.

* * * * *